United States Patent
Nag et al.

(10) Patent No.: US 12,195,441 B2
(45) Date of Patent: Jan. 14, 2025

(54) PARA ACYL SUBSTITUTED DIAZACYCLOHEXENE DERIVATIVES

(71) Applicant: Renovel Innovations, Inc., Fremont, CA (US)

(72) Inventors: Bishwajit Nag, Union City, CA (US);
Ananda Sen, Castro Valley, CA (US);
Nitish Nag, Union City, CA (US);
Arjun Sanyal, Castro Valley, CA (US);
Srinivasan Narasimhan, Chennai (IN)

(73) Assignee: Renovel Innovations, Inc., Fremont, CA (US)

( * ) Notice: Subject to any disclaimer, the term of this patent is extended or adjusted under 35 U.S.C. 154(b) by 0 days.

(21) Appl. No.: 18/387,620

(22) Filed: Nov. 7, 2023

(65) Prior Publication Data
US 2024/0101526 A1    Mar. 28, 2024

Related U.S. Application Data

(63) Continuation of application No. 17/499,728, filed on Oct. 12, 2021, now Pat. No. 11,807,619.

(60) Provisional application No. 63/141,889, filed on Jan. 26, 2021.

(51) Int. Cl.
| | | |
|---|---|---|
| C07D 339/08 | (2006.01) | |
| C07D 211/60 | (2006.01) | |
| C07D 401/12 | (2006.01) | |
| C07D 409/12 | (2006.01) | |

(52) U.S. Cl.
CPC .......... *C07D 339/08* (2013.01); *C07D 211/60* (2013.01); *C07D 401/12* (2013.01); *C07D 409/12* (2013.01)

(58) Field of Classification Search
CPC .. C07D 211/60; C07D 339/08; C07D 401/12; C07D 409/12
See application file for complete search history.

(56) References Cited

U.S. PATENT DOCUMENTS 11,807,619 B2 * 11/2023 Nag ..................... C07D 409/12

FOREIGN PATENT DOCUMENTS

IN     2013CH02367     * 12/2014

OTHER PUBLICATIONS

Muskinja, Mol Divers, (2016), vol. 20:591-604. (Year: 2016).*
Muskinja, Mol Divers, (2016), vol. 20; 591-604.
Bose, 2005, (III) p. 228-236, Arkivoc.
Bose, 2007, J Heterocyclic Chem, vol. 44, p. 211-214.
Kamal, E J Med Chem, 2011, vol. 46, p. 3274-3281.
Madduluri, Inorg Chem Comm, 2020, vol. 120, p. 1-6.
Mukhopadhyay, J Heterocyclic Chem, 2007, vol. 44, p. 979-981.
Nadalini, J Chromatography A, 2006, vol. 1126, p. 357-364.
Russowsky, Bioorg Chem, 2006, vol. 34, p. 173-182.
Singh, Catalysis Communications, 2006, vol. 7, p. 571-578.

\* cited by examiner

*Primary Examiner* — D Margaret M Seaman
(74) *Attorney, Agent, or Firm* — Adam Warwick Bell; Gregory Scott Smith

(57) ABSTRACT

Para-acyl substituted diazacyclohexenes, medical formulations thereof and methods for making and using the same.

21 Claims, 9 Drawing Sheets

Effect on Compound 1 on Body Weight in Male C57BL/6 Mice

Effect on Compound 1 on Body Weight in Male C57BL/6 Mice: % change

Effect on Compound 2 on Body Weight in Male C57BL/6 Mice

Effect on Compound 2 on Body Weight in Male C57BL/6 Mice: % change

PARA ACYL SUBSTITUTED DIAZACYCLOHEXENE DERIVATIVES

RELATIONSHIP TO OTHER APPLICATIONS

This patent is a continuation application claiming priority based on patent application Ser. No. 17/499,728 filed Oct. 12, 2021, which further claims the benefit of and priority to U.S. Provisional Application No. 63/141,894 filed Jan. 26, 2021, which is incorporated herein by reference.

FIELD OF THE INVENTION

The present invention relates to novel para-acyl substituted diazacyclohexene and derivatives thereof for use in the treatment of metabolic diseases, immunological diseases, inflammation, obesity, hyperlipidemia, hypertension, neurological diseases, and diabetes.

BACKGROUND

Metabolic syndrome, Insulin resistance syndrome or Syndrome X is a name for a group of risk factors that occur together and increase the risk for coronary artery disease, stroke, and type 2 diabetes. Metabolic syndrome is becoming more and more common globally specially in the United States. Researchers are not sure whether the syndrome is due to one single cause, but all the risks for the syndrome are related to obesity. The two most important risk factors for metabolic syndrome are: Extra weight around the middle and upper parts of the body (central obesity) and insulin resistance. The body uses insulin less effectively than normal. Insulin is needed to help control the amount of sugar in the body. As a result, blood sugar and fat levels rise. Other risk factors include Aging, Genes, Hormone changes, Lack of exercise. People who have metabolic syndrome often have two other problems that can either cause the condition or make it worse. Excess blood clotting, and increased levels of blood substances that are a sign of inflammation throughout the body.

Metabolic syndrome is affiliated with three or more of the following signs: Blood pressure equal to or higher than 130/85 mmHg, Fasting blood sugar (glucose) equal to or higher than 100 mg/dL, large waist circumference (length around the waist Men—40 inches or more and Women—35 inches or more, Low HDL cholesterol (Men—under 40 mg/dL Women—under 50 mg/dL) and Triglycerides equal to or higher than 150 mg/dL. In general, metabolic syndrome is a combination of Type 2 diabetes, obesity, hyperlipidemia and hypertension People with metabolic syndrome have an increased long-term risk for developing heart disease, type 2 diabetes, stroke, kidney disease, and poor blood supply to the legs. There is no one single treatment option available to treat metabolic syndrome. Current drugs that control blood glucose are usually not effective in lowering body weight, hypertension and cholesterol. Similarly, drugs that manage lipid levels may or may not have impact on other metabolic parameters. The present invention was aimed to develop new class of therapeutics derived, modified, and chemically synthesized from natural product which can combat multiple arms of metabolic syndrome. The invention also describes one such core group of molecules with synthesis scheme and biological data for diabetes, obesity, inflammation, hypertension and hyperlipidemia.

SUMMARY

The present invention relates to novel para-acyl substituted diazacyclohexene derivatives of the formula (I)

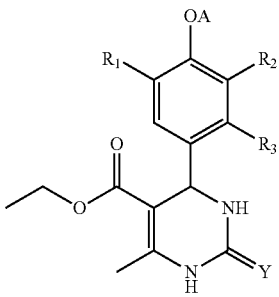

and to their analogs, their tautomeric forms, their stereoisomers, their polymorphs, their pharmaceutically acceptable salts, their pharmaceutically acceptable solvates, wherein $R_1$, $R_2$ and $R_3$ can be Hydrogen or alkoxy with straight chains or branched chains, Y can be selected from oxygen or sulphur and A can be derived from any straight chain or branched aliphatic acid chloride or from substituted or unsubstituted aryl or pyridyl acid chlorides.

The present invention also relates to a process for the preparation of the above said novel compounds, their analogs, their tautomeric forms, their stereoisomers, their polymorphs, their pharmaceutically acceptable salts, their pharmaceutically acceptable solvates, novel intermediates and pharmaceutical composites containing them. Tautomeric forms are isomeric forms which exists in a state of equilibrium capable of reacting according to either form. Stereoisomers include configurational isomers, such as cis- and trans double bonds, as well as optically active isomers having different spatial arrangements of their atoms. Polymorphs are molecules which can crystallize in two or more forms. Solvates are molecular or ionic complexes of molecules or ions of solvent with those of a solute. The amino acid derivatives are included, but not limited to naturally occurring amino acids. Analogs include those compounds which differ by substitution of an oxygen, sulphur, nitrogen or carbon atom in place of such an atom. Analogs also include atoms of the same family of the Periodic Table, such as F, Cl, Br and I. Derivatives include compounds resulting from routine functionalizing of atoms, such as, derivatives found by protecting amino or carboxyl groups by carboxylation or esterification, respectively.

DESCRIPTION

Figure 1A:
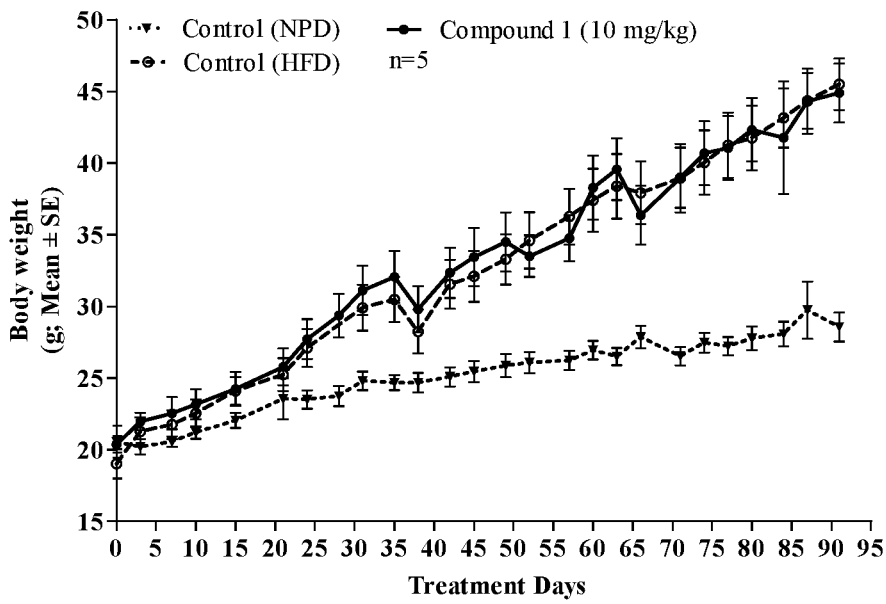
FIG. 1A shows the effect of compound 1 on body weight in male C57BL/6 mice when compared with the control high fat diet group.
Figure 1B:
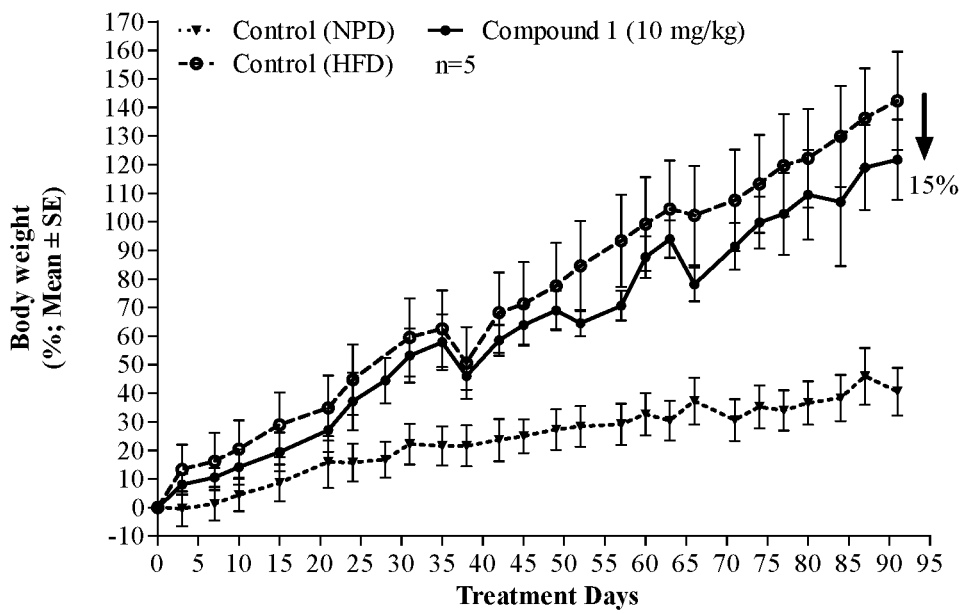
FIG. 1B shows that the group of mice treated with compound 1 showed a decrease by 15% in percent change in body weight compared with the control high fat diet group.
Figure 2A:
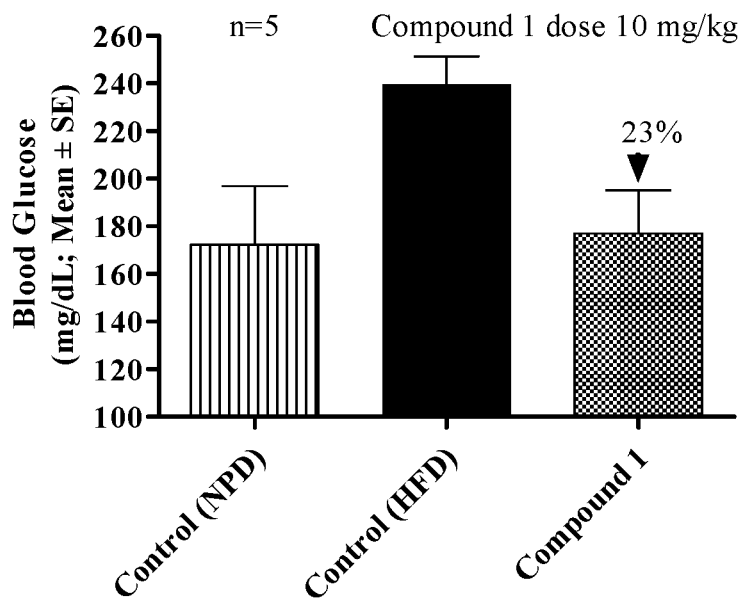
FIG. 2A shows that mice administered with compound 1 showed a significant (P<0.02) decrease by 26% in fasting blood glucose compared with the control high fat diet group.
Figure 2B:
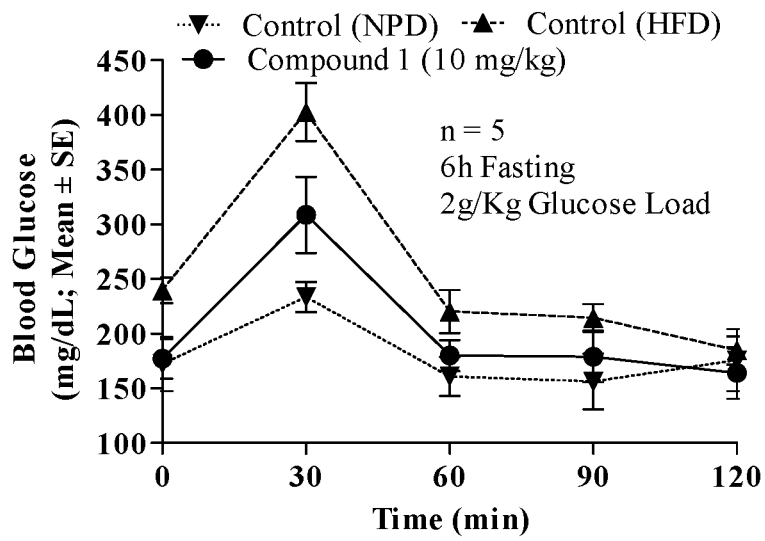
FIG. 2B shows the oral glucose tolerance test in C57BL/6 mice treated with compound 1 at 90 days.
Figure 2C:
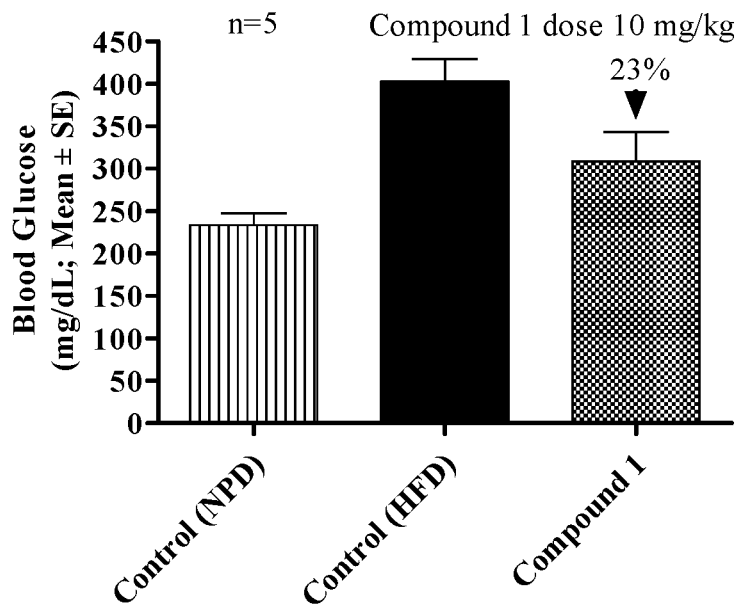
FIG. 2C shows that in the oral glucose tolerance test these mice also showed 23% reduction in blood glucose compared at the peak oral glucose tolerance test of 30 minutes compared with the control high fat diet group.
Figure 3:
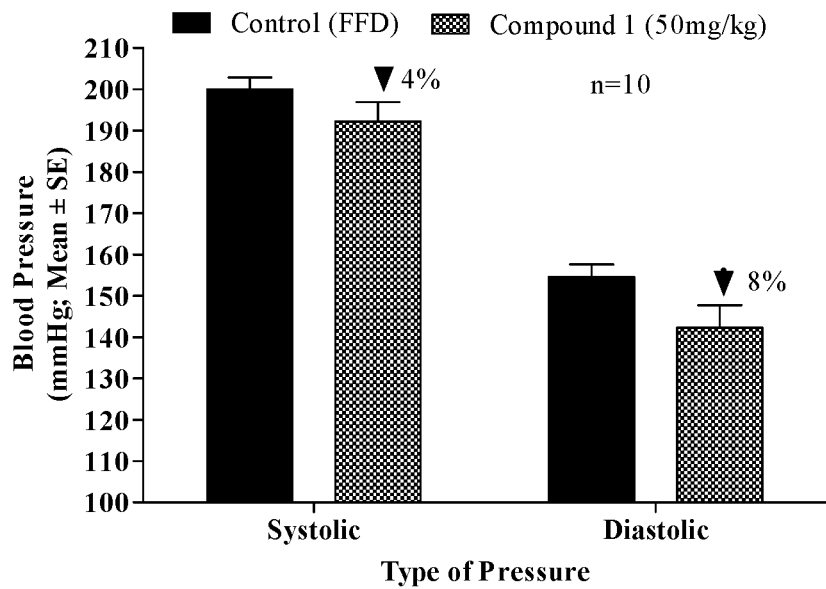
FIG. 3 shows that rats treated with compound 1 showed 4% decrease in systolic blood pressure and 8% decrease in diastolic blood pressure, when compared to the vehicle group.
Figure 4:
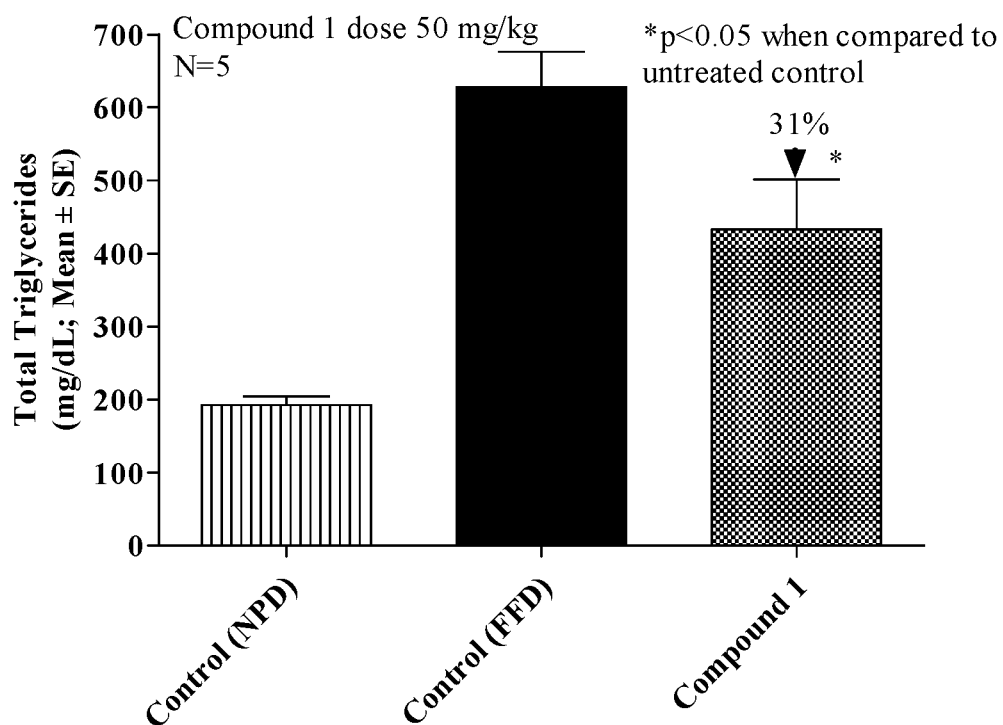
FIG. 4 shows that hamsters treated with compound 1 showed a significant decrease (P<0.05) by 31% in triglycerides compared with the high fructose fed group.
Figure 5:
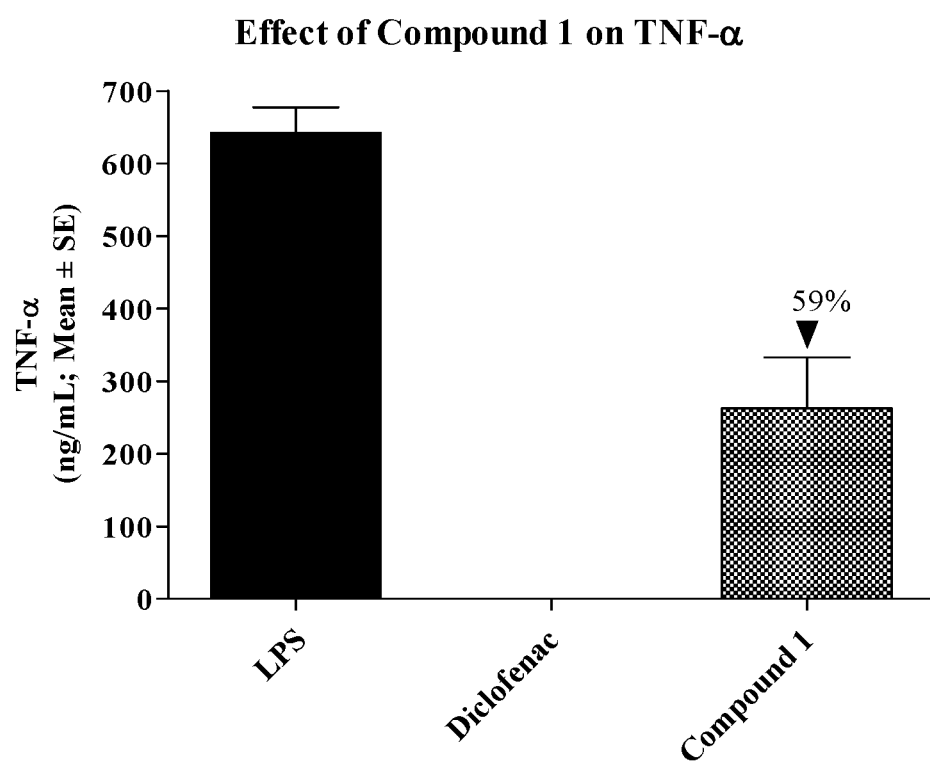
FIG. 5 shows that mice administered with compound 1 showed a 59% decrease of TNF-α from the LPS group.
Figure 6A:
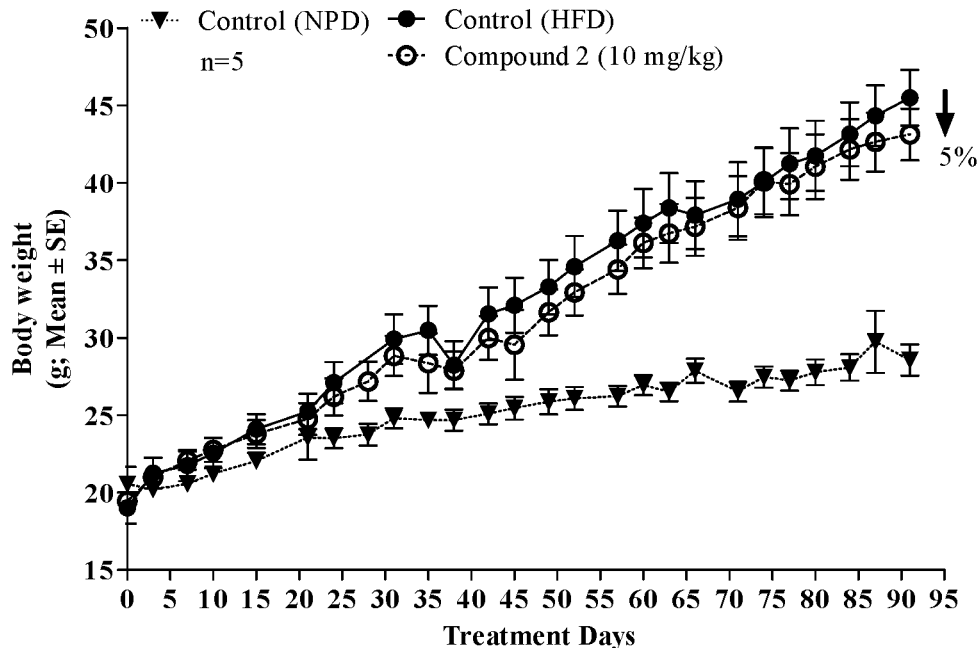
FIG. 6A shows that the C57BL/6 mice treated with compound 2 showed a 5% decrease in body weight when compared to the high fat diet control group.
Figure 6B:
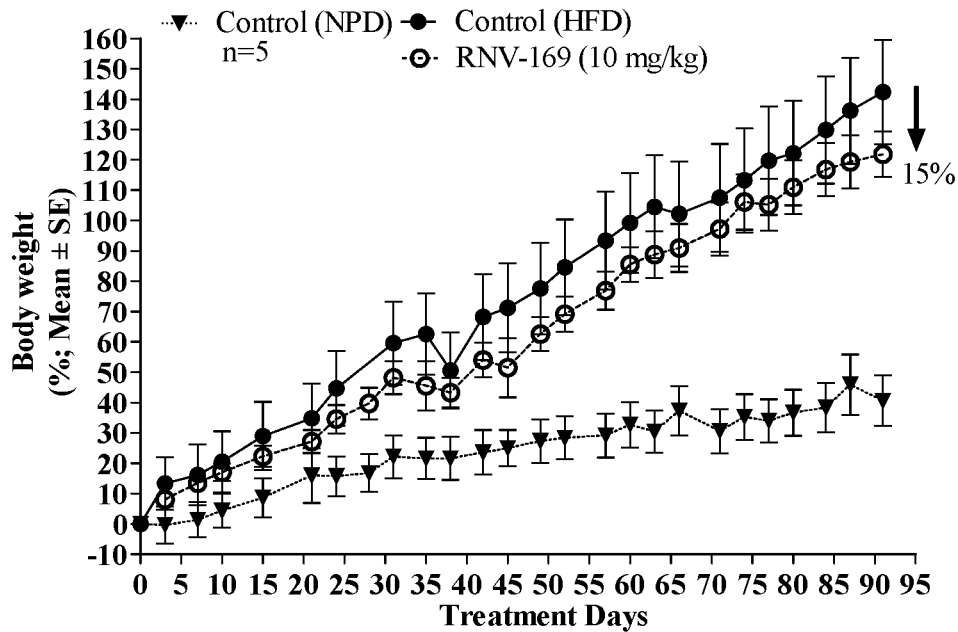
FIG. 6B shows that mice treated with compound 2 showed a significant (P<0.0001) decrease by 15% in body weight when compared to the high fat diet control group.
Figure 7A:
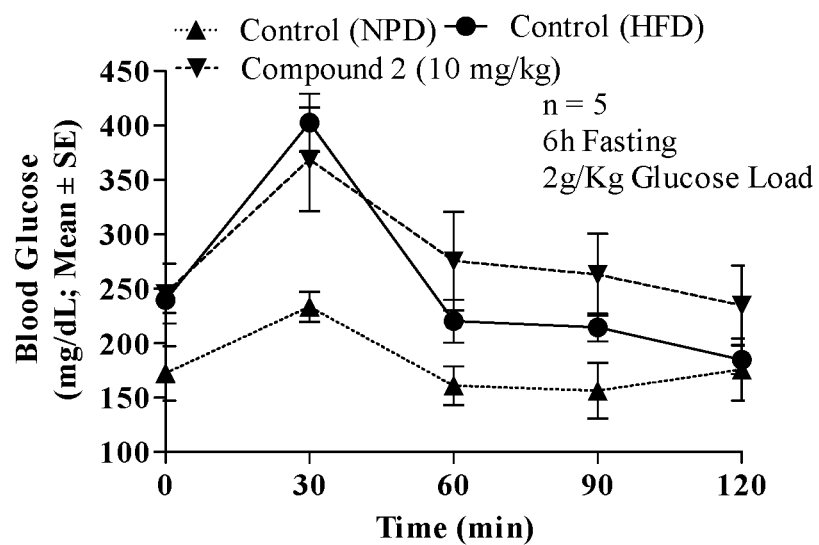
FIG. 7A shows the oral glucose tolerance test in C57BL/6 mice treated with compound 2 at 90 days.
Figure 7B:
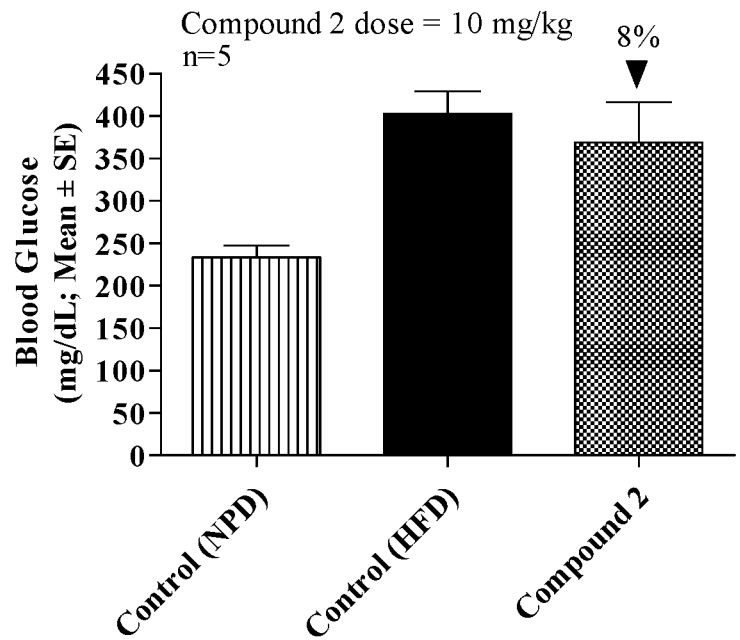
FIG. 7B shows that mice treated with compound 2 showed 8% reduction in blood glucose compared at the peak oral glucose tolerance test of 30 minutes compared with the control high fat diet group.
Figure 8A:
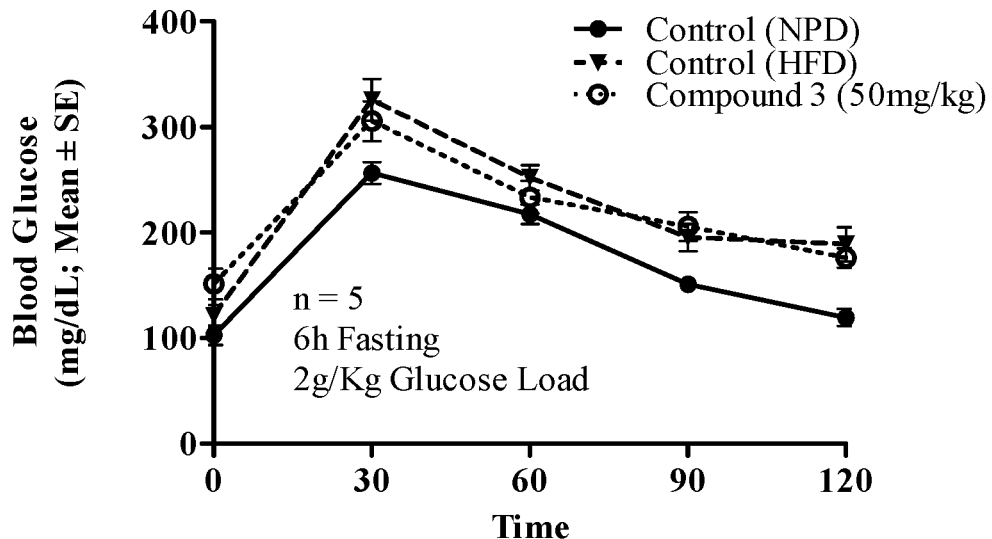
FIG. 8A shows the oral glucose tolerance test in C57BL/6 mice treated with compound 3 at 90 days.
Figure 8B:
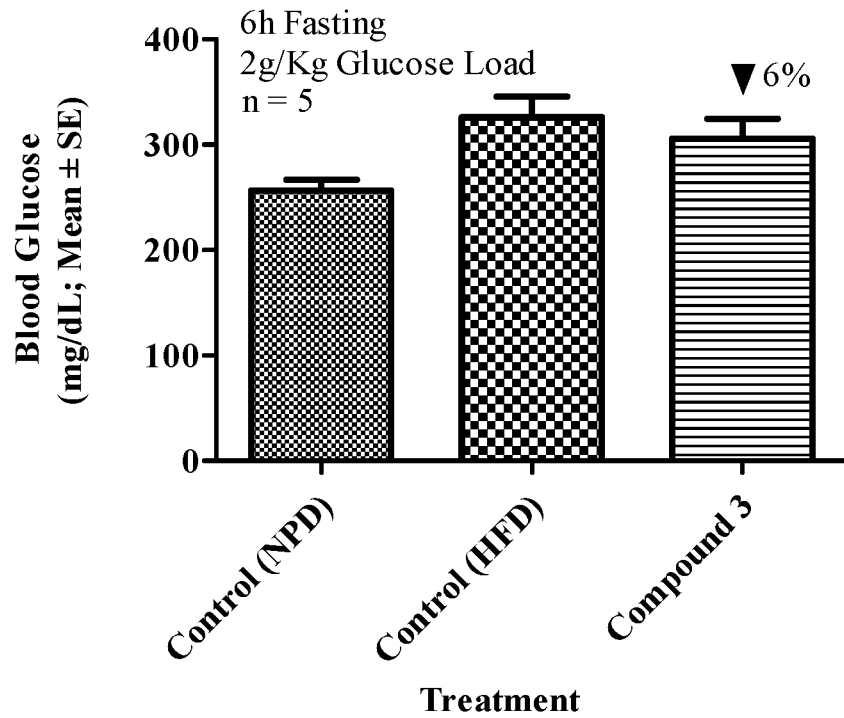
FIG. 8B shows that mice treated with compound 3 showed 6% reduction in blood glucose compared at the peak oral glucose tolerance test of 30 minutes compared with the control high fat diet group.
Figure 9A:
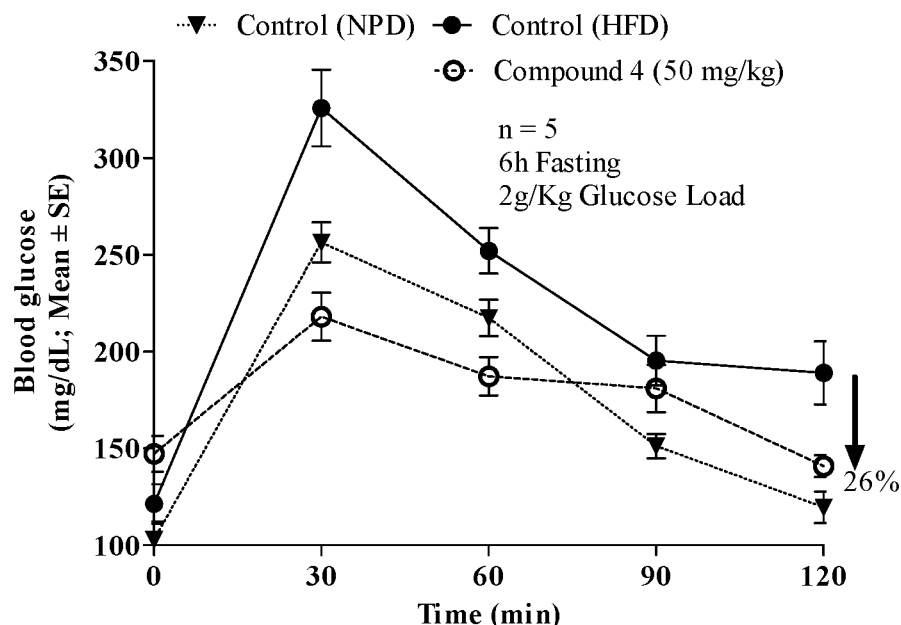
FIG. 9A shows that mice treated with compound 4 showed 26% reduction in blood glucose at 120 minutes after glucose administration.
Figure 9B:
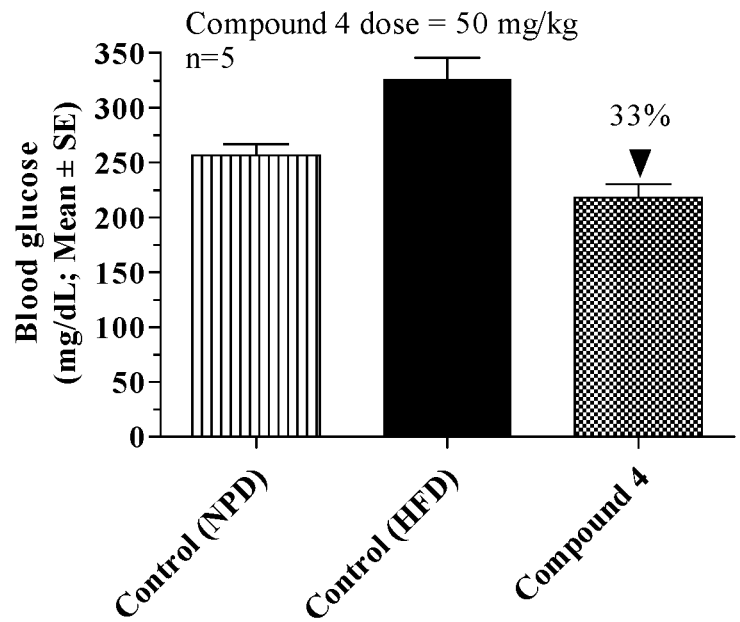
FIG. 9B showed a significant (P<0.001) reduction of 33% in blood glucose when compared at the peak oral glucose tolerance test of 30 minutes compared with the control high fat diet group.

In an embodiment of the present invention, the group represented as Riis selected from hydrogen and straight chain or branched alkoxy groups.

In an embodiment of the present invention, the group represented as $R_2$ and $R_3$ is predominantly hydrogen and can also be selected from halogens like fluorine, chlorine, bromine, iodine or astatine.

In an embodiment of the present invention, the group represented as Y can be selected from atoms such as oxygen or sulphur.

In an embodiment of the present invention, the group represented as A can be selected from derivatives of any straight chain or branched aliphatic acid chloride or from substituted or unsubstituted aryl or pyridyl acid chloride.

Pharmaceutically acceptable salts forming part of this invention include base addition salts such as alkali metal salts like Li, Na, and K salts, alkaline earth metal salts like Ca and Mg salts, salts of organic bases such as lysine, arginine, guanidine, diethanolamine, chlorine and the like, ammonium or substituted ammonium salts. Salts may include acid addition salts which are sulphates, nitrates, phosphates, perchlorates, borates, hydrohalides, acetates, tartarates, maleates, citrates, succinates, palmoates, methanesulphonates, benzoates, ascorbates, glycerophosphates, ketoglutarates and the like. Pharmaceutically acceptable solvates may be hydrates or comprising other solvents of crystallization such as alcohols.

More preferably, the present innovation relates to novel Para acyl substituted diazacyclohexene compounds of formula (I),

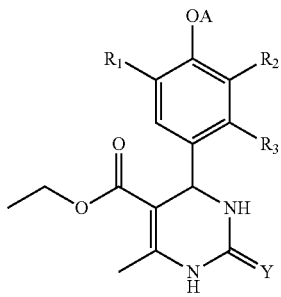

(I)

their derivatives, their analogs, their tautomeric forms, their stereoisomers, their polymorphs, their pharmaceutically acceptable salts, their pharmaceutically acceptable solvates, novel intermediates and pharmaceutical composites containing them, wherein, $R_1$ is predominantly straight chain alkoxy group or hydrogen, $R_2$ and $R_3$ are predominantly Hydrogen, Y is either oxygen or sulphur, and A can be selected from derivatives of any straight chain or branched aliphatic acid chloride or from substituted or unsubstituted aryl or pyridyl acid chloride.

The formula of the compounds synthesized in this present are listed below.

6-Methyl-2-oxo-4-[4-(3-phenyl-acryloyloxy)-phenyl]-1,2,3,4-tetrahydro-pyrimidine-5-carboxylic acid ethyl ester (Compound 2)

4-[3-Methoxy-4-(3-phenyl-acryloyloxy)-phenyl]-6-Methyl-2-oxo-1,2,3,4-tetrahydro-pyrimidine-5-carboxylic acid ethyl ester (compound 1)

4-(4-Isobutyryloxy-3-methoxy-phenyl)-6-methyl-2-oxo-1,2,3,4-tetrahydro-pyrimidine-5-carboxylic acid ethyl ester (compound 3)

4-(4-Isobutyryloxy-3-methoxy-phenyl)-6-methyl-2-thioxo-1,2,3,4-tetrahydro-pyrimidine-5-carboxylic acid ethyl ester (compound 4)

(E)-ethyl 4-(4-(cinnamoyloxy)phenyl)-6-methyl-2-oxo-1,2,3,4-tetrahydropyrimidine-5-carboxylate (E)-ethyl 4-(3-chloro-4-(cinnamoyloxy)phenyl)-6-methyl-2-oxo-1,2,3,4-tetrahydropyrimidine-5-carboxylate (E)-ethyl 4-(3-bromo-4-(cinnamoyloxy)phenyl)-6-methyl-2-oxo-1,2,3,4-tetrahydropyrimidine-5-carboxylate (E)-ethyl 4-(4-(cinnamoyloxy)-3-methoxyphenyl)-6-methyl-2-oxo-1,2,3,4-tetrahydropyrimidine-5-carboxylate (E)-ethyl 4-(3-chloro-4-(cinnamoyloxy)-5-methoxyphenyl)-6-methyl-2-oxo-1,2,3,4-tetrahydropyrimidine-5-carboxylate (E)-ethyl 4-(3-bromo-4-(cinnamoyloxy)-5-methoxyphenyl)-6-methyl-2-oxo-1,2,3,4-tetrahydropyrimidine-5-carboxylate (E)-ethyl 4-(4-(cinnamoyloxy)phenyl)-6-methyl-2-thioxo-1,2,3,4-tetrahydropyrimidine-5-carboxylate (E)-ethyl 4-(3-chloro-4-(cinnamoyloxy)phenyl)-6-methyl-2-thioxo-1,2,3,4-tetrahydropyrimidine-5-carboxylate (E)-ethyl 4-(3-bromo-4-(cinnamoyloxy)phenyl)-6-methyl-2-thioxo-1,2,3,4-tetrahydropyrimidine-5-carboxylate (E)-ethyl 4-(4-(cinnamoyloxy)-3-methoxyphenyl)-6-methyl-2-thioxo-1,2,3,4-tetrahydropyrimidine-5-carboxylate (E)-ethyl 4-(3-chloro-4-(cinnamoyloxy)-5-methoxyphenyl)-6-methyl-2-thioxo-1,2,3,4-tetrahydropyrimidine-5-carboxylate (E)-ethyl 4-(3-bromo-4-(cinnamoyloxy)-5-methoxyphenyl)-6-methyl-2-thioxo-1,2,3,4-tetrahydropyrimidine-5-carboxylate ethyl 4-(4-(isobutyryloxy)phenyl)-6-methyl-2-oxo-1,2,3,4-tetrahydropyrimidine-5-carboxylate ethyl 4-(3-chloro-4-(isobutyryloxy)phenyl)-6-methyl-2-oxo-1,2,3,4-tetrahydropyrimidine-5-carboxylate ethyl 4-(3-bromo-4-(isobutyryloxy)phenyl)-6-methyl-2-oxo-1,2,3,4-tetrahydropyrimidine-5-carboxylate ethyl 4-(4-(isobutyryloxy)-3-methoxyphenyl)-6-methyl-2-oxo-1,2,3,4-tetrahydropyrimidine-5-carboxylate ethyl 4-(3-chloro-4-(isobutyryloxy)-5-methoxyphenyl)-6-methyl-2-oxo-1,2,3,4-tetrahydropyrimidine-5-carboxylate ethyl 4-(3-bromo-4-(isobutyryloxy)-5-methoxyphenyl)-6-methyl-2-oxo-1,2,3,4-tetrahydropyrimidine-5-carboxylate ethyl 4-(4-(isobutyryloxy)phenyl)-6-methyl-2-thioxo-1,2,3,4-tetrahydropyrimidine-5-carboxylate ethyl 4-(3-chloro-4-(isobutyryloxy)phenyl)-6-methyl-2-thioxo-1,2,3,4-tetrahydropyrimidine-5-carboxylate ethyl 4-(3-bromo-4-(isobutyryloxy)phenyl)-6-methyl-2-thioxo-1,2,3,4-tetrahydropyrimidine-5-carboxylate ethyl 4-(4-(isobutyryloxy)-3-methoxyphenyl)-6-methyl-2-thioxo-1,2,3,4-tetrahydropyrimidine-5-carboxylate ethyl 4-(3-chloro-4-(isobutyryloxy)-5-methoxyphenyl)-6-methyl-2-thioxo-1,2,3,4-tetrahydropyrimidine-5-carboxylate ethyl 4-(3-bromo-4-(isobutyryloxy)-5-methoxyphenyl)-6-methyl-2-thioxo-1,2,3,4-tetrahydropyrimidine-5-carboxylate (E)-ethyl 6-methyl-2-oxo-4-(4-(3-(pyridin-4-yl)acryloyloxy)phenyl)-1,2,3,4-tetrahydropyrimidine-5-carboxylate (E)-ethyl 4-(3-chloro-4-(3-(pyridin-4-yl)acryloyloxy)phenyl)-6-methyl-2-oxo-1,2,3,4-tetrahydropyrimidine-5-carboxylate (E)-ethyl 4-(3-bromo-4-(3-(pyridin-4-yl)acryloyloxy)phenyl)-6-methyl-2-oxo-1,2,3,4-tetrahydropyrimidine-5-carboxylate (E)-ethyl 4-(3-methoxy-4-(3-(pyridin-4-yl)acryloyloxy)phenyl)-6-methyl-2-oxo-1,2,3,4-tetrahydropyrimidine-5-carboxylate (E)-ethyl 4-(3-chloro-5-methoxy-4-(3-(pyridin-4-yl)acryloyloxy)phenyl)-6-methyl-2-oxo-1,2,3,4-tetrahydropyrimidine-5-carboxylate (E)-ethyl 4-(3-bromo-5-methoxy-4-(3-(pyridin-4-yl)acryloyloxy)phenyl)-6-methyl-2-oxo-1,2,3,4-tetrahydropyrimidine-5-carboxylate (E)-ethyl 6-methyl-4-(4-(3-(pyridin-4-yl)acryloyloxy)phenyl)-2-thioxo-1,2,3,4-tetrahydropyrimidine-5-carboxylate (E)-ethyl 4-(3-chloro-4-(3-(pyridin-4-yl)acryloyloxy)phenyl)-6-methyl-2-thioxo-1,2,3,4-tetrahydropyrimidine-5-carboxylate (E)-ethyl 4-(3-bromo-4-(3-(pyridin-4-yl)acryloyloxy)phenyl)-6-methyl-2-thioxo-1,2,3,4-tetrahydropyrimidine-5-carboxylate (E)-ethyl 4-(3-methoxy-4-(3-(pyridin-4-yl)acryloyloxy)phenyl)-6-methyl-2-thioxo-1,2,3,4-tetrahydropyrimidine-5-carboxylate (E)-ethyl 4-(3-chloro-5-methoxy-4-(3-(pyridin-4-yl)acryloyloxy)phenyl)-6-methyl-2-thioxo-1,2,3,4-tetrahydropyrimidine-5-carboxylate (E)-ethyl 4-(3-bromo-5-methoxy-4-(3-(pyridin-4-yl)acryloyloxy)phenyl)-6-methyl-2-thioxo-1,2,3,4-tetrahydropyrimidine-5-carboxylate ethyl 6-methyl-4-(4-(4-methylpentanoyloxy)phenyl)-2-oxo-1,2,3,4-tetrahydropyrimidine-5-carboxylate ethyl 4-(3-chloro-4-(4-methylpentanoyloxy)phenyl)-6-methyl-2-oxo-1,2,3,4-tetrahydropyrimidine-5-carboxylate ethyl 4-(3-bromo-4-(4-methylpentanoyloxy)phenyl)-6-methyl-2-oxo-1,2,3,4-tetrahydropyrimidine-5-carboxylate ethyl 4-(3-methoxy-4-(4-methylpentanoyloxy)phenyl)-6-methyl-2-oxo-1,2,3,4-tetrahydropyrimidine-5-carboxylate ethyl 4-(3-chloro-5-methoxy-4-(4-methylpentanoyloxy)phenyl)-6-methyl-2-oxo-1,2,3,4-tetrahydropyrimidine-5-carboxylate ethyl 4-(3-bromo-5-methoxy-4-(4-methylpentanoyloxy)phenyl)-6-methyl-2-oxo-1,2,3,4-tetrahydropyrimidine-5-carboxylate ethyl 6-methyl-4-(4-(4-methylpentanoyloxy)phenyl)-2-thioxo-1,2,3,4-tetrahydropyrimidine-5-carboxylate ethyl 4-(3-chloro-4-(4-methylpentanoyloxy)phenyl)-6-methyl-2-thioxo-1,2,3,4-tetrahydropyrimidine-5-carboxylate ethyl 4-(3-bromo-4-(4-methylpentanoyloxy)phenyl)-6-methyl-2-thioxo-1,2,3,4-tetrahydropyrimidine-5-carboxylate ethyl 4-(3-methoxy-4-(4-methylpentanoyloxy)phenyl)-6-methyl-2-thioxo-1,2,3,4-tetrahydropyrimidine-5-carboxylate ethyl 4-(3-chloro-5-methoxy-4-(4-methylpentanoyloxy)phenyl)-6-methyl-2-thioxo-1,2,3,4-tetrahydropyrimidine-5-carboxylate ethyl 4-(3-bromo-5-methoxy-4-(4-methylpentanoyloxy)phenyl)-6-methyl-2-thioxo-1,2,3,4-tetrahydropyrimidine-5-carboxylate (E)-ethyl 6-methyl-2-oxo-4-(4-(3-o-tolylacryloyloxy)phenyl)-1,2,3,4-tetrahydropyrimidine-5-carboxylate (E)-ethyl 4-(3-chloro-4-(3-o-tolylacryloyloxy)phenyl)-6-methyl-2-oxo-1,2,3,4-tetrahydropyrimidine-5-carboxylate (E)-ethyl 4-(3-bromo-4-(3-o-tolylacryloyloxy)phenyl)-6-methyl-2-oxo-1,2,3,4-tetrahydropyrimidine-5-carboxylate (E)-ethyl 4-(3-methoxy-4-(3-o-tolylacryloyloxy)phenyl)-6-methyl-2-oxo-1,2,3,4-tetrahydropyrimidine-5-carboxylate (E)-ethyl 4-(3-chloro-5-methoxy-4-(3-o-tolylacryloyloxy)phenyl)-6-methyl-2-oxo-1,2,3,4-tetrahydropyrimidine-5-carboxylate (E)-ethyl 4-(3-bromo-5-methoxy-4-(3-o-tolylacryloyloxy)phenyl)-6-methyl-2-oxo-1,2,3,4-tetrahydropyrimidine-5-carboxylate (E)-ethyl 6-methyl-2-thioxo-4-(4-(3-o-tolylacryloyloxy)phenyl)-1,2,3,4-tetrahydropyrimidine-5-carboxylate (E)-ethyl 4-(3-chloro-4-(3-o-tolylacryloyloxy)phenyl)-6-methyl-2-thioxo-1,2,3,4-tetrahydropyrimidine-5-carboxylate (E)-ethyl 4-(3-bromo-4-(3-o-tolylacryloyloxy)phenyl)-6-methyl-2-thioxo-1,2,3,4-tetrahydropyrimidine-5-carboxylate (E)-ethyl 4-(3-methoxy-4-(3-o-tolylacryloyloxy)phenyl)-6-methyl-2-thioxo-1,2,3,4-tetrahydropyrimidine-5-carboxylate (E)-ethyl 4-(3-chloro-5-methoxy-4-(3-o-tolylacryloyloxy)phenyl)-6-methyl-2-thioxo-1,2,3,4-tetrahydropyrimidine-5-carboxylate (E)-ethyl 4-(3-bromo-5-methoxy-4-(3-o-tolylacryloyloxy)phenyl)-6-methyl-2-thioxo-1,2,3,4-tetrahydropyrimidine-5-carboxylate (E)-ethyl 4-(4-(3-(2-chloropyridin-4-yl)acryloyloxy)phenyl)-6-methyl-2-oxo-1,2,3,4-tetrahydropyrimidine-5-carboxylate (E)-ethyl 4-(3-chloro-4-(3-(2-chloropyridin-4-yl)acryloyloxy)phenyl)-6-methyl-2-oxo-1,2,3,4-tetrahydropyrimidine-5-carboxylate (E)-ethyl 4-(3-bromo-4-(3-(2-chloropyridin-4-yl)acryloyloxy)phenyl)-6-methyl-2-oxo-1,2,3,4-tetrahydropyrimidine-5-carboxylate (E)-ethyl 4-(4-(3-(2-chloropyridin-4-yl)acryloyloxy)-3-methoxyphenyl)-6-methyl-2-oxo-1,2,3,4-tetrahydropyrimidine-5-carboxylate (E)-ethyl 4-(3-chloro-4-(3-(2-chloropyridin-4-yl)acryloyloxy)-5-methoxyphenyl)-6-methyl-2-oxo-1,2,3,4-tetrahydropyrimidine-5-carboxylate (E)-ethyl 4-(3-bromo-4-(3-(2-chloropyridin-4-yl)acryloyloxy)-5-methoxyphenyl)-6-methyl-2-oxo-1,2,3,4-tetrahydropyrimidine-5-carboxylate (E)-ethyl 4-(4-(3-(2-chloropyridin-4-yl)acryloyloxy)phenyl)-6-methyl-2-thioxo-1,2,3,4-tetrahydropyrimidine-5-carboxylate (E)-ethyl 4-(3-chloro-4-(3-(2-chloropyridin-4-yl)acryloyloxy)phenyl)-6-methyl-2-thioxo-1,2,3,4-tetrahydropyrimidine-5-carboxylate (E)-ethyl 4-(3-bromo-4-(3-(2-chloropyridin-4-yl)acryloyloxy)phenyl)-6-methyl-2-thioxo-1,2,3,4-tetrahydropyrimidine-5-carboxylate (E)-ethyl 4-(4-(3-(2-chloropyridin-4-yl)acryloyloxy)-3-methoxyphenyl)-6-methyl-2-thioxo-1,2,3,4-tetrahydropyrimidine-5-carboxylate (E)-ethyl 4-(3-chloro-4-(3-(2-chloropyridin-4-yl)acryloyloxy)-5-methoxyphenyl)-6-methyl-2-thioxo-1,2,3,4-tetrahydropyrimidine-5-carboxylate (E)-ethyl 4-(3-bromo-4-(3-(2-chloropyridin-4-yl)acryloyloxy)-5-methoxyphenyl)-6-methyl-2-thioxo-1,2,3,4-tetrahydropyrimidine-5-carboxylate The list also consists of the IUPAC names of the compounds given the table below—

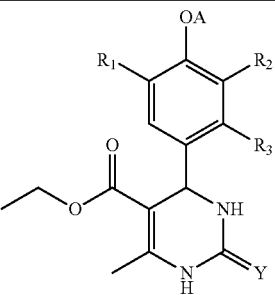

| S.No | A | Y | $R_1$ ($R_3$=H) | $R_2$ |
|---|---|---|---|---|
| 1. | cinnamoyl | O | H | H |
| 2. | cinnamoyl | O | H | Cl |
| 3. | cinnamoyl | O | H | Br |
| 4. | cinnamoyl | O | $OCH_3$ | H |
| 5. | cinnamoyl | O | $OCH_3$ | Cl |
| 6. | cinnamoyl | O | $OCH_3$ | Br |
| 7. | cinnamoyl | S | H | H |
| 8. | cinnamoyl | S | H | Cl |
| 9. | cinnamoyl | S | H | Br |
| 10 | cinnamoyl | S | $OCH_3$ | H |
| 11 | cinnamoyl | S | $OCH_3$ | Cl |

-continued

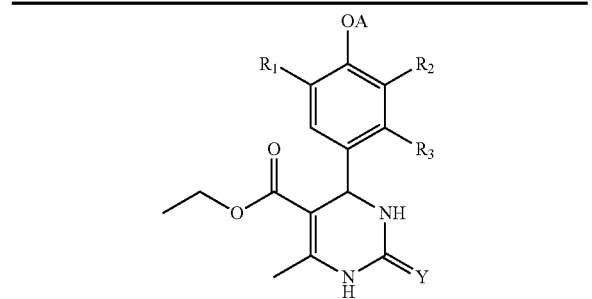

| S.No | A | Y | R₁ (R₃=H) | R₂ |
|---|---|---|---|---|
| 12 | cinnamoyl (PhCH=CH-C(=O)-) | S | OCH₃ | Br |
| 13 | isobutyryl | O | H | H |
| 14 | isobutyryl | O | H | Cl |
| 15 | isobutyryl | O | H | Br |
| 16 | isobutyryl | O | OCH₃ | H |
| 17 | isobutyryl | O | OCH₃ | Cl |
| 18 | isobutyryl | O | OCH₃ | Br |
| 19 | isobutyryl | S | H | H |
| 20 | isobutyryl | S | H | Cl |
| 21 | isobutyryl | S | H | Br |

-continued

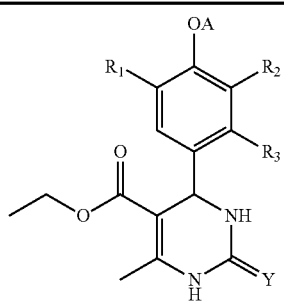

| S.No | A | Y | R₁ (R₃=H) | R₂ |
|---|---|---|---|---|
| 22 | isobutyryl | S | OCH₃ | H |
| 23 | isobutyryl | S | OCH₃ | Cl |
| 24 | isobutyryl | S | OCH₃ | Br |
| 25 | 3-(pyridin-4-yl)acryloyl | O | H | H |
| 26 | 3-(pyridin-4-yl)acryloyl | O | H | Cl |
| 27 | 3-(pyridin-4-yl)acryloyl | O | H | Br |
| 28 | 3-(pyridin-4-yl)acryloyl | O | OCH₃ | H |
| 29 | 3-(pyridin-4-yl)acryloyl | O | OCH₃ | Cl |

-continued

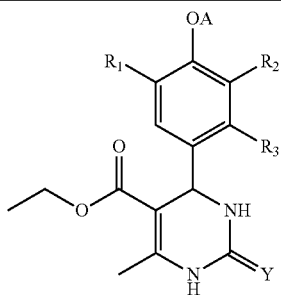

R₃=H

| S.No | A | Y | R₁ | R₂ |
|---|---|---|---|---|
| 30 | (E)-4-pyridyl-CH=CH-C(O)- | O | OCH₃ | Br |
| 31 | (E)-4-pyridyl-CH=CH-C(O)- | S | H | H |
| 32 | (E)-4-pyridyl-CH=CH-C(O)- | S | H | Cl |
| 33 | (E)-4-pyridyl-CH=CH-C(O)- | S | H | Br |
| 34 | (E)-4-pyridyl-CH=CH-C(O)- | S | OCH₃ | H |
| 35 | (E)-4-pyridyl-CH=CH-C(O)- | S | OCH₃ | Cl |
| 36 | (E)-4-pyridyl-CH=CH-C(O)- | S | OCH₃ | Br |
| 37 | 4-methylpentanoyl | O | H | H |

-continued

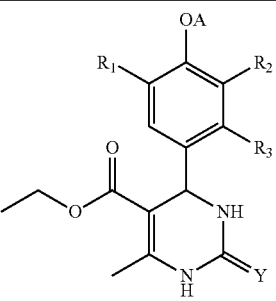

R₃=H

| S.No | A | Y | R₁ | R₂ |
|---|---|---|---|---|
| 38 | 4-methylpentanoyl | O | H | Cl |
| 39 | 4-methylpentanoyl | O | H | Br |
| 40 | 4-methylpentanoyl | O | OCH₃ | H |
| 41 | 4-methylpentanoyl | O | OCH₃ | Cl |
| 42 | 4-methylpentanoyl | O | OCH₃ | Br |
| 43 | 4-methylpentanoyl | S | H | H |
| 44 | 4-methylpentanoyl | S | H | Cl |
| 45 | 4-methylpentanoyl | S | H | Br |
| 46 | 4-methylpentanoyl | S | OCH₃ | H |

-continued

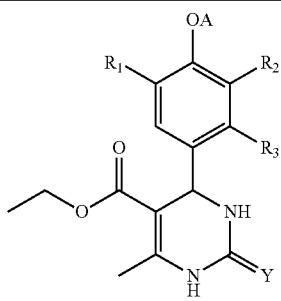
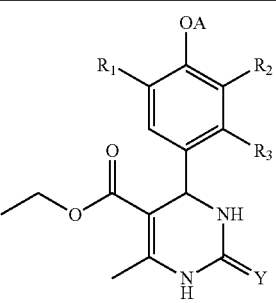

| S.No | A | Y | R₃=H R₁ | R₂ |
|---|---|---|---|---|
| 47 | (isopentyl ketone) | S | OCH₃ | Cl |
| 48 | (isopentyl ketone) | S | OCH₃ | Br |
| 49 | (o-methyl cinnamoyl) | O | H | H |
| 50 | (o-methyl cinnamoyl) | O | H | Cl |
| 51 | (o-methyl cinnamoyl) | O | H | Br |
| 52 | (o-methyl cinnamoyl) | O | OCH₃ | H |
| 53 | (o-methyl cinnamoyl) | O | OCH₃ | Cl |
| 54 | (o-methyl cinnamoyl) | O | OCH₃ | Br |
| 55 | (o-methyl cinnamoyl) | S | H | H |
| 56 | (o-methyl cinnamoyl) | S | H | Cl |
| 57 | (o-methyl cinnamoyl) | S | H | Br |
| 58 | (o-methyl cinnamoyl) | S | OCH₃ | H |
| 59 | (o-methyl cinnamoyl) | S | OCH₃ | Cl |
| 60 | (o-methyl cinnamoyl) | S | OCH₃ | Br |
| 61 | (2-chloropyridin-4-yl acryloyl) | O | H | H |

-continued

[Structure: ethyl 4-(4-OA-3-R2-5-R1-phenyl)-6-methyl-2-Y-1,2,3,4-tetrahydropyrimidine-5-carboxylate]

R3=H

| S.No | A | Y | R1 | R2 |
|---|---|---|---|---|
| 62 | (E)-3-(2-chloropyridin-4-yl)acryloyl | O | H | Cl |
| 63 | (E)-3-(2-chloropyridin-4-yl)acryloyl | O | H | Br |
| 64 | (E)-3-(2-chloropyridin-4-yl)acryloyl | O | OCH3 | H |
| 65 | (E)-3-(2-chloropyridin-4-yl)acryloyl | O | OCH3 | Cl |
| 66 | (E)-3-(2-chloropyridin-4-yl)acryloyl | O | OCH3 | Br |
| 67 | (E)-3-(2-chloropyridin-4-yl)acryloyl | S | H | H |
| 68 | (E)-3-(2-chloropyridin-4-yl)acryloyl | S | H | Cl |
| 69 | (E)-3-(2-chloropyridin-4-yl)acryloyl | S | H | Br |
| 70 | (E)-3-(2-chloropyridin-4-yl)acryloyl | S | OCH3 | H |
| 71 | (E)-3-(2-chloropyridin-4-yl)acryloyl | S | OCH3 | Cl |
| 72 | (E)-3-(2-chloropyridin-4-yl)acryloyl | S | OCH3 | Br |

Preferred salts for the compounds listed above are hydrochloride, hydrobromide, sodium, potassium, or magnesium.

According to another feature of this present invention, there is provided a process for the preparation of the compound represented by the formula I, wherein all symbols are as defined as earlier, as shown in scheme I Scheme 1

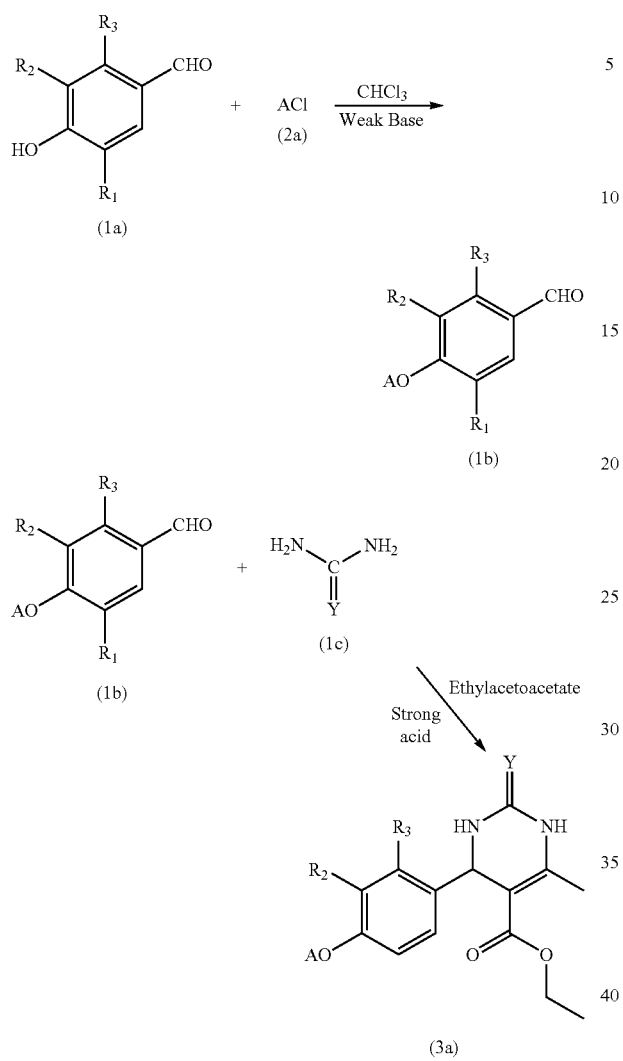

(ACl is always an acid chloride where A can be branched or straight chain aliphatic, aryl or pyridyl derivatives)

The reaction of a compound of general formula (1a) with a compound of general formula (2a) may be carried out using a polar protic solvent which may be selected from chloroform, ethanol, ethyl acetate and the like and in the presence of weak bases like DEA, TEA, Isopropyl amine, pyridine, piperidine and the like, but more preferably with chloroform solvent and the base TEA. The reaction temperature may vary from 0 to 100° C., preferably in the range of 60-80° C., and the duration may range from 15 minutes to 5 hours. The product is obtained by suitable work up procedures like water and alkali washing and solvent concentration. The resulting compound has general formula (1b).

The reaction of a compound of general formula (1b) with a compound of general formula (1c) may be carried out in the presence of a polar protic solvent such as an alcohol which may be selected from methanol, ethanol, propanol and the likes. The reaction is always carried out in the presence of ethylacetoacetate and can be catalyzed by strong acids such as sulfuric acid. The reaction temperature can vary between 5-100° C., preferably being in the range of 60-80° C. and the duration may range from 15 minutes to 5 hours and the final product may be precipitated directly or obtained by suitable work up procedures like water and alkali wash and solvent concentration. The end compound has general formula (3a).

The invention is explained in detail in the examples given below which are provided by way of illustration only and therefore should not be construed to limit the scope of the invention.

Example 1

Synthesis of 6-Methyl-2-oxo-4-[4-(3-phenyl-acryloyloxy)-phenyl]-1,2,3,4-tetrahydro-pyrimidine-5-carboxylic acid ethyl ester (compound 1)

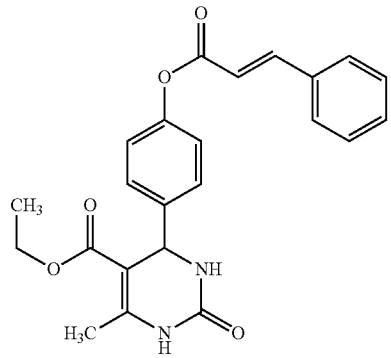 [SMILES: CCOC(=O)C1=C(C)NC(=O)NC1c1ccc(OC(=O)/C=C/c2ccccc2)cc1]

Step (i)

Synthesis of Cinnamoyl Chloride

Cinnamic acid (50.0 g) was taken in a clean and dry three neck round bottom flask and thionyl chloride (175 ml) was added drop wise with constant stirring. The reaction mixture was refluxed at 70-80° C. for five hours. After reflux the excess thionyl chloride was distilled off. Hexane was added and distillation was performed again to remove any traces of thionyl chloride. The product was then transferred to an amberlite bottle and stored. (Yield 53.0 g).

Step (ii)

Synthesis of 3-phenyl-acrylic acid-4-formyl-phenyl ester 4-hydroxy benzaldehyde (14.69 g) was taken in a clean and dry two neck round bottom flask and chloroform (200 ml) was added with constant stirring. After the reaction mixture was cooled to 5-10° C., cinnamoyl chloride (20.0 g) was added drop wise. Stirring was continued for 15 minutes following which triethylamine (16.44 ml) was introduced. The reaction was allowed to proceed for 4 hours. It was then transferred into a beaker and washed twice with water (2×250 ml). The separated chloroform layer was shaken with 10% NaOH solution (2×250 ml), and then dried over anhydrous sodium sulphate. The chloroform was evaporated under reduced pressure and the precipitated solid was filtered and dried. 3-phenyl-acrylic acid-4-formyl-phenyl ester yield 15.70 g.

Step (ii)

Synthesis of Methyl-2-oxo-4-[4-(3-phenyl-acryloyloxy)-phenyl]-1,2,3,4-tetrahydro-pyrimidine-5-carboxylic acid ethyl ester 3-phenyl-acrylic acid-4-formyl-phenyl ester (3.0 g) was taken in a clean and dry round bottom flask. Urea (0.71 g), ethylacetoacetate (1.54 ml) and methanol (50 ml) were added to it. Catalytic amount of concentrated sulfuric acid was added carefully and the reaction mixture was refluxed at 60-80° C. for 5 hours. The reaction was then quenched by transferring the mixture into a beaker containing water. The solid product precipitated was filtered, washed with hexane and dried. Methyl-2-oxo-4-[4-(3-phenyl-acryloyloxy)-phenyl]-1,2,3,4-tetrahydro-pyrimidine-5-carboxylic acid ethyl ester was produced with a yield of 1.20 g.

NMR—7.64 (1H, d), 7.14-7.30 (aromatic, m), 6.90-7.10 (aromatic, m), 6.40 (1H, d), 6.01 (2H, s), 5.56 (1H, d), 4.19 (2H, m), 1.71 (3H, s), 1.30 (3H, t).

Example 2

Synthesis of 4-[3-Methoxy-4-(3-phenyl-acryloyloxy)-phenyl]-6-Methyl-2-oxo-1,2,3,4-tetrahydro-pyrimidine-5-carboxylic acid ethyl ester (compound 2)

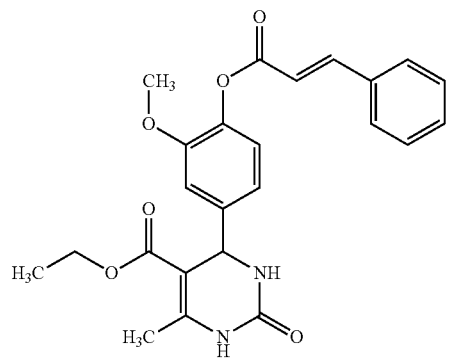 [SMILES: CCOC(=O)C1=C(C)NC(=O)NC1c1ccc(OC(=O)/C=C/c2ccccc2)c(OC)c1]

Step (i)

Synthesis of Cinnamoyl Chloride

Cinnamic acid (50.0 g) was taken in a clean and dry three neck round bottom flask and thionyl chloride (175 ml) was added drop wise with constant stirring. The reaction mixture was refluxed at 70-80° C. for five hours. After reflux the excess thionyl chloride was distilled off. Hexane was added and distillation was performed again to remove any traces of thionyl chloride. The product was then transferred to an amberlite bottle and stored. (Yield 53.0 g)

Step (ii)

Synthesis of Cinnamoyl Vanillin

Vanillin (22.8 g) was taken in a clean and dry round bottom flask and chloroform (200 ml) was added whilst stirring. The reaction mixture was cooled to 5-10° C. Cinnamoyl chloride (25.0 g) was added drop wise. Stirring was continued for another 15 minutes and TEA (20.55 ml) was added drop wise. The reaction was allowed to continue for 5 hours with constant stirring. The reaction mixture was then transferred to a 1 L beaker and washed twice with water (2×250 ml). The chloroform layer was separated and further washed with 10% NaOH solution (2×250 ml) and then dried with anhydrous sodium sulphate. The chloroform layer was then filtered and concentrated under vacuum. Hexane was then added to the concentrated chloroform layer and the solid formed was filtered and dried. (Yield 16.2 g)

Step (iii)

Synthesis of 4-[3-Methoxy-4-(3-phenyl-acryloyloxy)-phenyl]-6-Methyl-2-oxo-1,2,3,4-tetrahydro-pyrimidine-5-carboxylic acid ethyl ester Cinnamoyl vanillin (3.0 g) was taken in a clean and dry round bottom flask. Urea (0.64 g), ethylacetoacetate (2.56 ml) and methanol (50 ml) were added to it. Catalytic amount of concentrated sulfuric acid was added carefully and the reaction mixture was refluxed at 60-80° C. for 5 hours. The reaction was then quenched by transferring the mixture into a beaker containing water. The solid product precipitated was filtered, washed with hexane and dried. 4-[3-Methoxy-4-(3-phenyl-acryloyloxy)-phenyl]-6-Methyl-2-oxo-1,2,3,4-tetrahydro-pyrimidine-5-carboxylic acid ethyl ester yield (1.42 g).

NMR—7.64 (1H, d), 7.14-7.30 (aromatic, m), 6.40-6.60 (aromatic, m), 6.40 (1H, d), 6.01 (2H, s), 5.56 (1H, d), 4.19 (2H, m), 3.74 (3H, s), 1.71 (3H, s), 1.30 (3H, t)

Example 3

Synthesis of 4-(4-Isobutyryloxy-3-methoxy-phenyl)-6-methyl-2-oxo-1,2,3,4-tetrahydro-pyrimidine-5-carboxylic acid ethyl ester (compound 3)

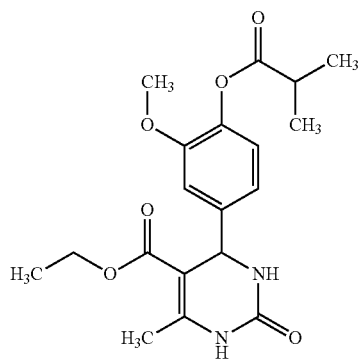 [SMILES: CCOC(=O)C1=C(C)NC(=O)NC1c1ccc(OC(=O)C(C)C)c(OC)c1]

Step (i)

Vanillin isobutyrate (3.0 g) was taken in a clean and dry round bottom flask. Urea (0.81 g), ethylacetoacetate (2.16 ml) and methanol (50 ml) were added to it. Catalytic amount of concentrated sulfuric acid was added carefully and the reaction mixture was refluxed at 60-80° C. for 5 hours. The reaction was then quenched by transferring the mixture into a beaker containing water. The solid product precipitated was filtered, washed with hexane and dried. 4-(4-Isobutyryloxy-3-methoxy-phenyl)-6-methyl-2-oxo-1,2,3,4-tetra-hydro-pyrimidine-5-carboxylic acid ethyl ester was produced with a yield of 1.35 g.

NMR—δ0.50-6.85 (aromatic, m), 6.00 (2H, m), 4.19 (2H, m), 3.75 (2H, m), 2.67 (1H, m), 1.70 (3H, s), 1.30 (3H, t), 1.14 (6H, d)

Example 4

Synthesis of 4-(4-Isobutyryloxy-3-methoxy-phenyl)-6-methyl-2-thioxo-1,2,3,4-tetrahydro-pyrimidine-5-carboxylic acid ethyl ester (compound 4)

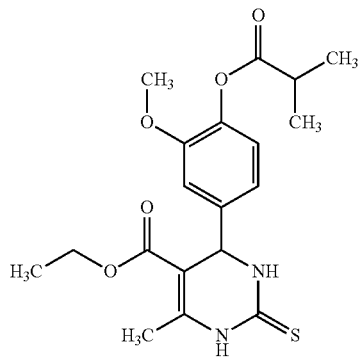

Step (i)

Vanillin isobutyrate (3.0 g) was taken in a clean and dry round bottom flask. Thiourea (1.02 g), ethylacetoacetate (2.29 ml) and methanol (50 ml) were added to it. Catalytic amount of concentrated sulfuric acid was added carefully and the reaction mixture was refluxed at 60-80° C. for 5 hours. The reaction was then quenched by transferring the mixture into a beaker containing water. The solid product precipitated was filtered, washed with hexane and dried of 4-(4-Isobutyryloxy-3-methoxy-phenyl)-6-methyl-2-thioxo-1,2,3,4-tetrahydro-pyrimidine-5-carboxylic acid ethyl ester yield (1.50 g).

NMR—δ0.50-6.85 (aromatic, m), 4.19 (2H, m), 3.75 (2H, m), 2.67 (1H, m), 2.0 (2H, m), 1.70 (3H, s), 1.30 (3H, t), 1.14 (6H, d).

GENERAL DISCLOSURES

This specification incorporates by reference all documents referred to herein and all documents filed concurrently with this specification or filed previously in connection with this application, including but not limited to such documents which are open to public inspection with this specification. All numerical quantities mentioned herein include quantities that may be plus or minus 20% of the stated amount in every case, including where percentages are mentioned. As used in this specification, the singular forms "a, an", and "the" include plural reference unless the context clearly dictates otherwise. Thus, for example, a reference to "a part" includes a plurality of such parts, and so forth. The term "comprises" and grammatical equivalents thereof are used in this specification to mean that, in addition to the features specifically identified, other features are optionally present. For example, a composition "comprising" (or "which comprises") ingredients A, B and C can contain only ingredients A, B and C, or can contain not only ingredients A, B and C but also one or more other ingredients. The term "consisting essentially of" and grammatical equivalents thereof is used herein to mean that, in addition to the features specifically identified, other features may be present which do not materially alter the claimed invention. The term "at least" followed by a number is used herein to denote the start of a range beginning with that number (which may be a range having an upper limit or no upper limit, depending on the variable being defined). For example, "at least 1" means 1 or more than 1, and "at least 80%" means 80% or more than 80%. The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40%" means 40% or less than 40%. Where reference is made in this specification to a method comprising two or more defined steps, the defined steps can be carried out in any order or simultaneously (except where the context excludes that possibility), and the method can optionally include one or more other steps which are carried out before any of the defined steps, between two of the defined steps, or after all the defined steps (except where the context excludes that possibility). When, in this specification, a range is given as "(a first number) to (a second number)" or "(a first number)-(a second number)", this means a range whose lower limit is the first number and whose upper limit is the second number. For example, "from 40 to 70 microns" or "40-70 microns" means a range whose lower limit is 40 microns, and whose upper limit is 70 microns.

The invention claimed is:
1. A compound of formula (I)

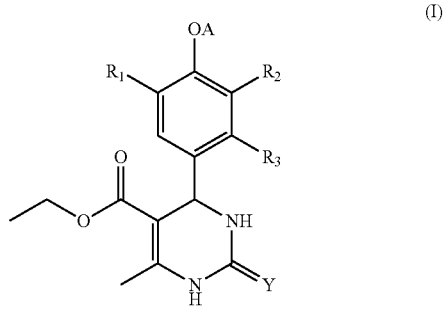

wherein
R1 is H or OCH3
R2 is H
R3 is H
Y is O or S,
and wherein A is selected from the group consisting of:

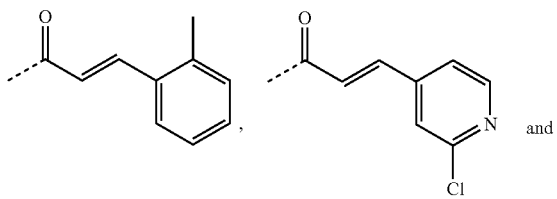

-continued and a pharmaceutically acceptable salt of said compound.

2. A method for inducing a physiological effect or treating a disease in a subject, selected from the group consisting of: reducing free fatty acid in plasma, reducing cholesterol in plasma, and reducing triglyceride levels in plasma, the method comprising administering to a subject in need thereof an effective amount of a compound comprising:

formula (I)

(I)

wherein
R1 is H or OCH3
R2 is H
R3 is H
Y is O or S,
and wherein A is selected from the group consisting of:

and a pharmaceutically acceptable salt of said compound.

3. The method of claim 2, for reducing free fatty acid in plasma comprising administering an effective amount of the compound of claim 1 to a patient in need thereof.

4. The method of claim 2, for reducing cholesterol in plasma comprising administering an effective amount of the compound of claim 1 to a patient in need thereof.

5. The method of claim 2, for reducing triglyceride levels in plasma comprising administering an effective amount of the compound of claim 1 to a patient in need thereof.

6. The method of claim 2, for treating inflammation comprising administering an effective amount of the compound of claim 1 to a patient in need thereof.

7. The compound of claim 1 comprising the structure as follows (compound S. No. 13)

Chemical Formula: $C_{18}H_{22}N_2O_5$
Molecular Weight: 346.38
ethyl 4-(4-(isobutyryloxy)phenyl)-6-methyl-2-oxo-1,2,3,4-tetrahydropyrimidine-5-carboxylate.

8. The compound of claim 1 comprising the structure as follows (compound S. No. 19)

Chemical Formula: $C_{18}H_{22}N_2O_4S$
Molecular Weight: 362.44
ethyl 4-(4-(isobutyryloxy) phenyl)-6-methyl-2-thioxo-1,2,3,4-tetrahydropyrimidine-5-carboxylate.

9. The compound of claim 1 comprising the structure as follows (compound S. No. 37)

Chemical Formula: $C_{20}H_{26}N_2O_5$
Molecular Weight: 374.43
ethyl 6-methyl-4-(4-((4-methylpentanoyl)oxy)phenyl)-2-oxo-1,2,3,4-tetrahydropyrimidine-5-carboxylate.

10. The compound of claim 1 comprising the structure as follows (compound S. No. 40)

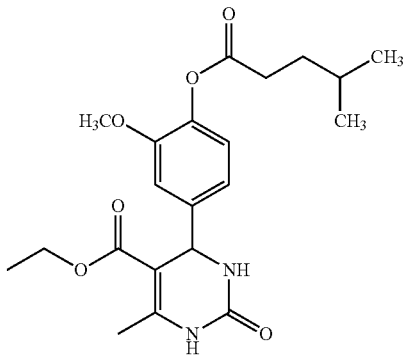

Chemical Formula: $C_{21}H_{28}N_2O_6$
Molecular Weight: 404.46
ethyl 4-(3-methoxy-4-((4-methylpentanoyl)oxy)phenyl)-6-methyl-2-oxo-1,2,3,4-tetrahydropyrimidine-5-carboxylate.

11. The compound of claim 1 comprising the structure as follows (compound S. No. 43)

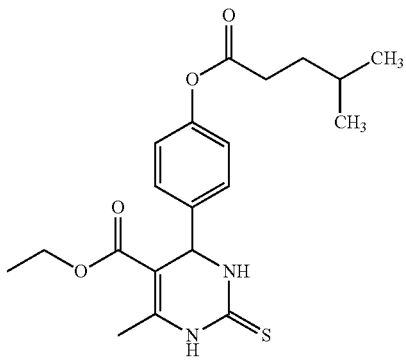 [SMILES: CCOC(=O)C1=C(C)NC(=O)NC1c1ccc(OC(=O)CCC(C)C)cc1]

Chemical Formula: $C_{20}H_{26}N_2O_4S$
Molecular Weight: 390.501
ethyl 6-methyl-4-(4-((4-methylpentanoyl)oxy)phenyl)-2-thioxo-1,2,3,4-tetrahydropyrimidine-5-carboxylate.

12. The compound of claim 1 comprising the structure as follows (compound S. No. 46)

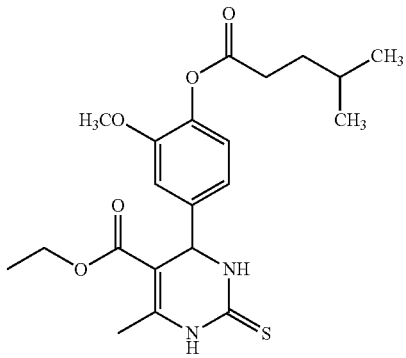 [SMILES: CCOC(=O)C1=C(C)NC(=S)NC1c1ccc(OC(=O)CCC(C)C)c(OC)c1]

Chemical Formula: $C_{21}H_{28}N_2O_5S$
Molecular Weight: 420.52
ethyl 4-(3-methoxy-4-((4-methylpentanoyl)oxy)phenyl)-6-methyl-2-thioxo-1,2,3,4-tetrahydropyrimidine-5-carboxylate.

13. The compound of claim 1 comprising the structure as follows (compound S. No. 49)

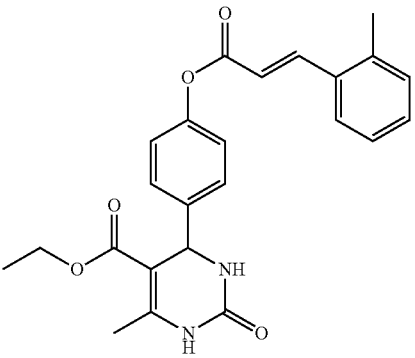 [SMILES: CCOC(=O)C1=C(C)NC(=O)NC1c1ccc(OC(=O)/C=C/c2ccccc2C)cc1]

Chemical Formula: $C_{24}H_{24}N_2O_5$
Molecular Weight: 420.46
(E)-ethyl 6-methyl-2-oxo-4-(4-((3-(o-tolyl)acryloyl)oxy)phenyl)-1,2,3,4-tetrahydropyrimidine-5-carboxylate.

14. The compound of claim 1 comprising the structure as follows (compound S. No. 52)

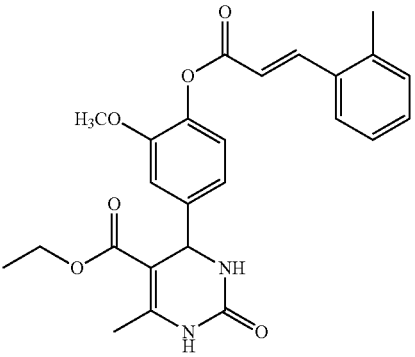

Chemical Formula: $C_{25}H_{26}N_2O_6$
Molecular Weight: 450.48
(E)-ethyl 4-(3-methoxy-4-((3-(o-tolyl)acryloyl)oxy)phenyl)-6-methyl-2-oxo- 1,2,3,4-tetrahydropyrimidine-5-carboxylate.

15. The compound of claim 1 comprising the structure as follows (compound S. No. 55)

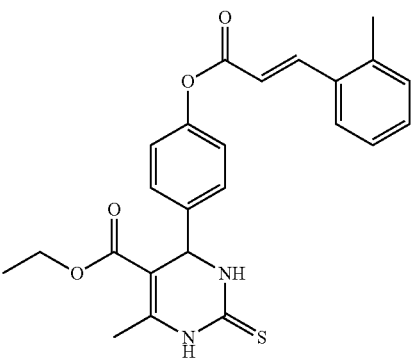 [SMILES: CCOC(=O)C1=C(C)NC(=S)NC1c1ccc(OC(=O)/C=C/c2ccccc2C)cc1]

Chemical Formula: $C_{24}H_{24}N_2O_4S$
Molecular Weight: 436.52
(E)-ethyl 6-methyl-2-thioxo-4-(4-((3-(o-tolyl)acryloyl)oxy)phenyl)-1,2,3,4-tetrahydropyrimidine-5-carboxylate.

16. The compound of claim 1 comprising the structure as follows (compound S. No. 58)

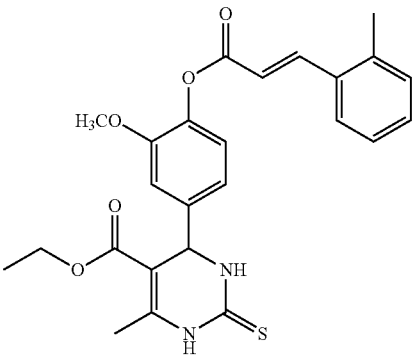 [SMILES: CCOC(=O)C1=C(C)NC(=S)NC1c1ccc(OC(=O)/C=C/c2ccccc2C)c(OC)c1]

Chemical Formula: $C_{25}H_{26}N_2O_5S$
Molecular Weight: 466.55

(E)-ethyl 4-(3-methoxy-4-((3-(o-tolyl)acryloyl)oxy)phenyl)-6-methyl-2-thioxo-1,2,3,4-tetrahydropyrimidine-5-carboxylate.

17. The compound of claim 1 comprising the structure as follows (compound S. No. 61)

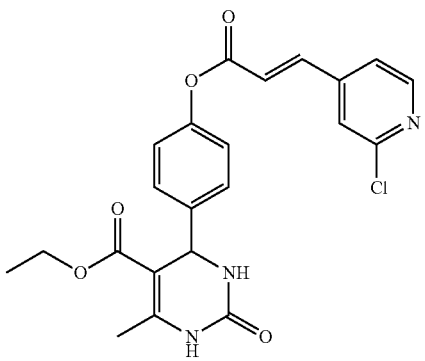 [SMILES: CCOC(=O)C1=C(C)NC(=O)NC1c1ccc(OC(=O)/C=C/c2ccnc(Cl)c2)cc1]

Chemical Formula: $C_{22}H_{20}ClN_3O_5$
Molecular Weight: 441.86

(E)-ethyl 4-(4-((3-(2-chloropyridin-4-yl)acryloyl)oxy)phenyl)-6-methyl-2-oxo-1,2,3,4-tetrahydropyrimidine-5-carboxylate.

18. The compound of claim 1 comprising the structure as follows (compound S. No. 64)

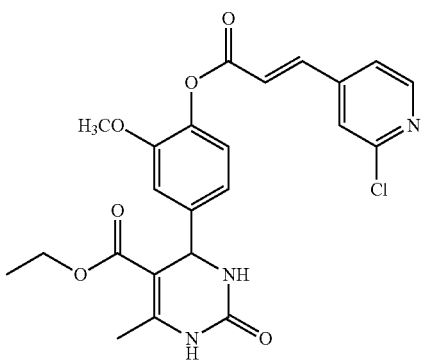 [SMILES: CCOC(=O)C1=C(C)NC(=O)NC1c1ccc(OC(=O)/C=C/c2ccnc(Cl)c2)c(OC)c1]

Chemical Formula: $C_{23}H_{22}ClN_3O_6$
Molecular Weight: 471.89

(E)-ethyl 4-(4-((3-(2-chloropyridin-4-yl)acryloyl)oxy)-3-methoxyphenyl)-6-methyl-2-oxo-1,2,3,4-tetrahydropyrimidine-5-carboxylate.

19. The compound of claim 1 comprising the structure as follows (compound S. No. 67)

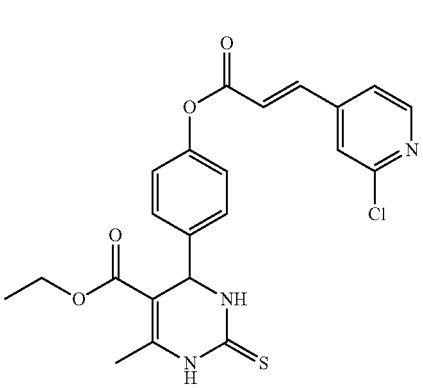

Chemical Formula: $C_{22}H_{20}ClN_3O_4S$
Molecular Weight: 457.93

(E)-ethyl 4-(4-((3-(2-chloropyridin-4-yl)acryloyl)oxy)phenyl)-6-methyl-2-thioxo-1,2,3,4-tetrahydropyrimidine-5-carboxylate.

20. The compound of claim 1 comprising the structure as follows (compound S. No. 70)

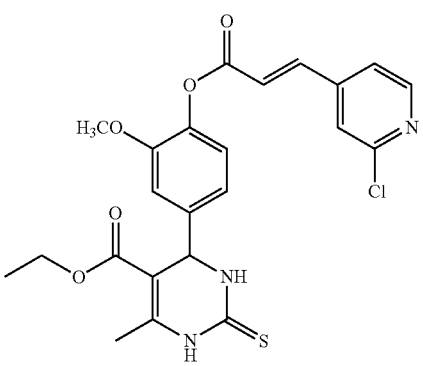

Chemical Formula: $C_{23}H_{22}ClN_3O_5S$
Molecular Weight: 487.96

(E)-ethyl 4-(4-((3-(2-chloropyridin-4-yl)acryloyl)oxy)-3-methoxyphenyl)-6-methyl-2-thioxo-1,2,3,4-tetrahydropyrimidine-5-carboxylate.

21. A method for reducing blood glucose in a subject, the method comprising administering to a subject in need thereof an effective amount of a compound comprising:
formula (I)

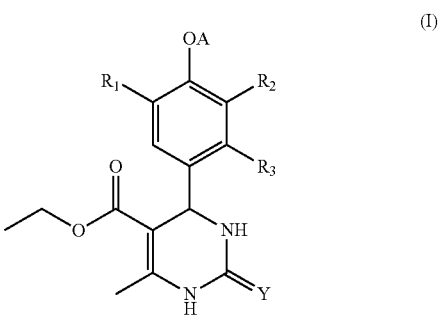

wherein
R1 is OCH3
R2 is H
R3 is H
Y is O or S,
and wherein A is
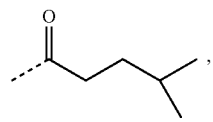
and a pharmaceutically acceptable salt of said compound.
* * * * *